(12) United States Patent
Ciok et al.

(10) Patent No.: US 7,846,144 B2
(45) Date of Patent: Dec. 7, 2010

(54) OSTOMY APPLIANCE

(75) Inventors: Danuta Ciok, Nivaa (DK); Esben Stroebech, Hoersholm (DK); Flemming Moss, Vedbaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/541,823

(22) PCT Filed: Jan. 12, 2004

(86) PCT No.: PCT/DK2004/000011

§ 371 (c)(1), (2), (4) Date: Jul. 11, 2005

(87) PCT Pub. No.: WO2004/062536

PCT Pub. Date: Jul. 29, 2004

(65) Prior Publication Data

US 2006/0184145 A1     Aug. 17, 2006

(30) Foreign Application Priority Data

Jan. 10, 2003     (DK) .............................. 2003 00018

(51) Int. Cl.
*A61F 5/44* (2006.01)
(52) U.S. Cl. .................. 604/344; 604/332; 604/338
(58) Field of Classification Search .................. 604/332, 604/337–339, 342–344
See application file for complete search history.

(56) References Cited

U.S. PATENT DOCUMENTS

| | | | |
|---|---|---|---|
| 4,095,599 A | 6/1978 | Simonet-Haibe | |
| 4,367,732 A | 1/1983 | Poulsen et al. | |
| 5,051,259 A | 9/1991 | Olsen et al. | |
| 5,714,225 A | 2/1998 | Hansen et al. | |
| 5,800,415 A | 9/1998 | Olsen | |
| 6,726,791 B1 | 4/2004 | Øelund et al. | |
| 6,764,474 B2 | 7/2004 | Nielsen et al. | |

FOREIGN PATENT DOCUMENTS

| | | |
|---|---|---|
| EP | 1 117 516 | 7/2001 |
| GB | 2 290 974 A | 1/1996 |
| GB | 2 351 238 A | 12/2000 |
| WO | WO 89/05619 | 6/1989 |
| WO | WO 93/18725 | 9/1993 |
| WO | WO 94/18919 | 9/1994 |

(Continued)

*Primary Examiner*—Melanie J Hand
(74) *Attorney, Agent, or Firm*—Coloplast Corp., Coloplast A/S; Daniel G. Chapik; Nicholas R. Bauman

(57) ABSTRACT

An ostomy appliance body side member or an ostomy appliance including an adhesive wafer having a first adhesive surface for securing the appliance to the user's skin, and a second surface provided with a hydrophobic adhesive. The part of the adhesive wafer surrounding the stoma shows balanced plastic and elastic properties allowing the hole of the ostomy appliance to be enlarged by rolling up the inner rim around the hole to form a torus. The torus is locked in the rolled up position by adhesion between the hydrophobic adhesive on the second surface and the first adhesive surface, the hydrophobic adhesive ensuring that the torus does not unroll even when the first adhesive surface is exposed to moisture, thereby reducing the risk of causing injury to or constriction of the stoma.

4 Claims, 3 Drawing Sheets

FOREIGN PATENT DOCUMENTS

| WO | WO 98/17212 | 4/1998 |
| WO | WO 98/53771 | 12/1998 |
| WO | WO 9853771 A1 * | 12/1998 |
| WO | WO 00/18554 | 4/2000 |
| WO | WO 00/25709 | 5/2000 |

* cited by examiner

OSTOMY APPLIANCE

This is a nationalization of PCT/DK04/000011 filed Jan. 12, 2004 and published in English.

BACKGROUND OF THE INVENTION

1. Field of the Invention

The present invention relates to an ostomy appliance body side member, an ostomy appliance comprising such body side member, to an ostomy sealing member, to a one-piece ostomy appliance, and to methods of applying an ostomy appliance body side member or a one-piece ostomy appliance around a stoma.

In connection with surgery for a number of diseases in the gastro-intestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearers abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may e.g. be a system se comprising matching coupling rings or matching flanges and adhesive surfaces engaging with and sealing against a flange area of the body side member.

It is necessary to change the body side member of a two-piece appliance when the centre part of the adhesive wafer has been sufficiently deteriorated to allow access of the aggressive exudates to the skin surrounding the stoma, irrespective of the fact that the wafer as such has a much longer wearing time. The access of aggressive exudates to the skin is causing skin problems.

Frequent changing of the body side member of a two-piece appliance is undesirable due to the irritation of the skin and the quality of life of the user may be improved and the nuisance of the wearing of an ostomy appliance reduced if the intervals between exchanging of body side member can be increased.

The service time of the body side ostomy member depends inter alia of the amount and the aggressiveness of the exudates and of the sealing between the stoma and the body side ostomy member.

The sealing depends on the fit to the stoma. Conventionally, only a limited number of standard appliances having holes of different size are available and the user or an assistant must customise the body side member by cutting the edge of the hole to adapt the body side member to the stoma. However, the resulting hole may show an exposed edge which may injure the surface of the stoma e.g. when the user bends or turns due to the exposed edge of the carrier sheet which after cutting even may show a serrated edge.

2. Description of the Related Art

Published International Patent Application No. WO 98/53771 discloses an ostomy appliance comprising a body side member comprising an adhesive wafer for securing the appliance to the users skin, said wafer having a hole for receiving a stoma, and an optionally separately exchangeable receiving member or bag secured to the body side ostomy member for receiving secretions from the ostomy said ostomy appliance further comprising a sealing member disposed in the hole of the wafer surrounding the stoma wherein the sealing member disposed in the hole of the wafer surrounding the stoma, said sealing member having a hole for accommodating the stoma and said sealing member having balanced plastic and elastic properties allowing a better adaptation of the hole of the ostomy appliance to a stoma by a temporary enlarging the hole by everting or rolling up the inner rim of the hole for accommodating the stoma.

When the ostomy appliance disclosed in WO 98/53771 has been placed over and around a stoma the adhesive sealing member may recover essentially to the original form to fit snugly to the stoma. The "release" may be performed using e.g. a finger or more or less automatically due to influence by elastic force, heat and/or humidity causing the sealing member to essentially resume its original shape.

However, there is still a risk of constriction of the stoma due to elastic properties of the adhesive forming the wafer, which may cause harm to the stoma and which cannot be controlled after application.

Thus, there is still a need for a sealing against a stoma ensuring that no leak occurs at the rim of the stoma in order to prolong the service time of the appliance, which ensures an easy adaptation to the actual user and at the same time reduces the risk of causing injury to or constriction of the stoma.

SUMMARY OF THE INVENTION

The invention relates to an ostomy appliance body side member comprising an adhesive wafer having a first adhesive surface for securing the appliance to the user's skin, said wafer having a second surface being covered with a carrier sheet which wafer has a hole for receiving a stoma wherein the part of the adhesive wafer surrounding the stoma shows balanced plastic and elastic properties allowing an adaptation of the size of the hole of the ostomy appliance to a stoma by enlarging the hole by rolling up the inner rim thereof for accommodating the stoma.

The invention furthermore relates to an ostomy sealing member in the form of a mouldable mass or ring which shows a sufficient adhesiveness to adhere to the skin and seal around an ostomy and between the ostomy and an ostomy appliance adapted to receive secretions from the stoma, which sealing member shows a sufficient cohesion to be removed in one piece, independently of removal of the ostomy appliance body side member without leaving remaining adhesive on the skin or the ostomy appliance, said sealing member having a hole for accommodating a stoma and said sealing member having balanced plastic and elastic properties allowing an enlarging of the hole for receiving a stoma by rolling the inner rim of the hole.

Still further, the invention relates to a one-piece ostomy appliance comprising an adhesive wafer having a first adhesive surface for securing the appliance to the user's skin, said wafer having a second surface being covered with a carrier sheet to which a receiving bag is secured, which wafer has a hole for receiving a stoma wherein the part of the adhesive wafer surrounding the stoma shows balanced plastic and elastic properties allowing an adaptation of the size of the hole of the ostomy appliance to a stoma.

Still further, the invention relates to a methods for applying an ostomy body side member, an ostomy sealing member or a one-piece ostomy appliance comprising an adhesive wafer having a first surface for securing the appliance to the user's skin, said wafer having a second surface being covered with a carrier sheet which wafer has a hole for receiving a stoma wherein the part of the adhesive wafer surrounding the stoma shows balanced plastic and elastic properties allowing an adaptation of the size of the hole of the ostomy appliance to a stoma.

BRIEF DESCRIPTION OF THE DRAWINGS

The invention is disclosed more in detail with reference to the drawings in which.

DETAILED DESCRIPTION OF THE PRESENT INVENTION

Figure 1:
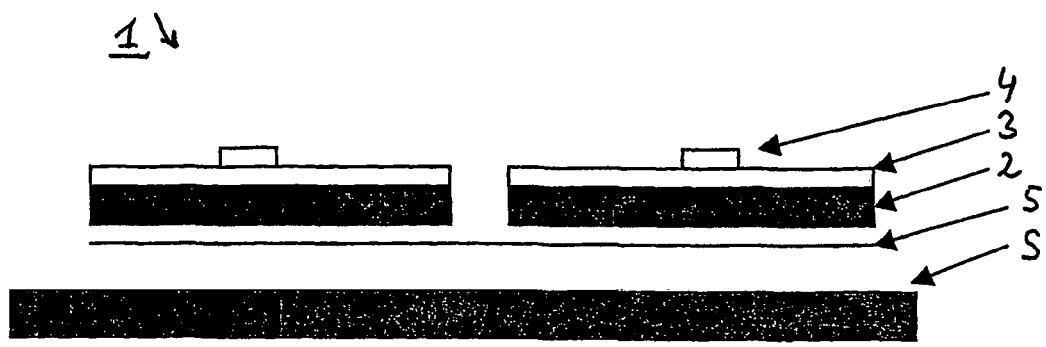
FIG. 1 shows a cross sectional view of a state of the art body side member.

The present invention relates to an ostomy appliance body side member comprising an adhesive wafer having a first adhesive surface for securing the appliance to the user's skin, said wafer having a second surface being covered with a carrier sheet which wafer has a hole for receiving a stoma wherein a part of the adhesive wafer surrounding the stoma shows balanced plastic and elastic properties allowing an adaptation of the size of the hole of the ostomy appliance to a stoma by enlarging the hole for accommodating the stoma by rolling up the inner rim thereof forming a torus and wherein a part of the second surface of the wafer surrounding the hole shows surface properties compatible with the first adhesive surface of the adhesive wafer locking the torus to the second surface in its rolled position by the contact between the second surface and the first adhesive surface.

The ostomy appliance of the invention provides an ostomy appliance enabling a simple, safe and reliable customisation of the hole of a body side member without the use of tools and at the same time reduces the risk of causing injury to or constriction of the stoma.

The elastic properties of the area around the hole of a body side member, a sealing member, or a one-piece ostomy appliance according to the invention and the adhesiveness of the adhesive surface products are chosen to ensure that when rolling up the inner rim of the hole, a torus is formed, and the torus will for practical purposes be locked in its rolled position by the contact to the surface surrounding the stoma and the torus will not unroll.

The present invention provides a freedom in the choice of the adhesive having the most suitable adhesive properties without having to consider the elasticity of the adhesive. Thus, a very elastic adhesive may be used, which is often desirable as such adhesives often show a high degree of cohesion rendering it more easy to remove the adhesive without leaving residues on the skin and also often show a higher resistance to leaching of constituents of the adhesive prolonging the service time of the body side member. Furthermore, the edge of a carrier sheet will be covered by the rolled adhesive layer, which will then constitute the surface contacting the stoma, and thus, direct contact between the edge and the surface of the stoma is avoided.

It is preferred that the adhesive wafer is made from an adhesive comprising hydrocolloids for providing a capacity for absorbing humidity for prolonging the service time. The use of a hydrocolloid-containing adhesive will also provide for an automatic sealing against the surface of the stoma after rolling the edge of the hole of the ostomy appliance due to the expansion of the adhesive upon absorption of humidity.

In one embodiment of the invention the part of the second surface surrounding the hole shows adhesive properties compatible with the first adhesive surface of the adhesive wafer.

In a preferred embodiment the second surface of a part of the carrier sheet surrounding the stoma is provided with a hydrophobic adhesive.

A hydrophobic adhesive not comprising water-absorbing constituents is more stable against the action of aggressive exudates, which will delay the deterioration of the adhesive wafer, especially when the entire surface within the boundaries of the coupling is covered. In a preferred embodiment of the invention the hydrophobic adhesive loses its adhesiveness when wetted with exudates from the stoma. Thus, incidental movements of the stoma will not expand the hole of the body side member permanently and the risk of adhesion of the wall of a collecting bag to the distal surface is avoided.

The second adhesive surface is preferably protected by a release liner until the application of the body side member.

In another preferred embodiment of the invention, the carrier sheet on a central part of the second surface of the adhesive wafer surrounding the stoma is provided with a weakening pattern reducing the stiffness of the area for facilitating a rolling thereof. Such a pattern will weaken the carrier sheet and enable a change of the length or stretching in a tangential direction of the material forming a torus when rolling the edge of a hole of an appliance of the invention and enabling an increase of the circumference of the torus during the rolling as the carrier sheet itself must show a pronounced stiffness in order to be able to serve as mechanical stable anchoring for a coupling ring or a receiving bag. This embodiment of the invention may e.g. be based on a state of the art body side member by providing the carrier sheet on a central part of the second surface of the adhesive wafer surrounding the stoma with a weakening pattern reducing the stiffness of the area for facilitating a rolling thereof.

The weakening pattern may e.g. be in the form of weakening lines or perforations and may suitably be made by punching or cutting. The pattern is preferably in the form of holes or cuts penetrating the carrier sheet for facilitating the rolling of the edge.

The weakening pattern may be provided using any suitable manner known per se for providing cuts through an outer layer of a sandwich construction, e.g. using mechanical cutting or punching tools or using laser cutting.

In another preferred embodiment the carrier sheet is absent on a part of the second surface of the adhesive wafer surrounding the stoma. This embodiment provides in itself for a thinner area next to the central hole facilitating the rolling of the edge and also eliminates the stiffness provided by the carrier sheet in this area.

In this embodiment, the adhesive surface on the second surface of the adhesive wafer may be constituted of the second surface itself, especially if the exposed second surface is an adhesive showing slow absorption of humidity, or a second layer of adhesive may be disposed in this area. When using a hydrophobic adhesive it is preferred that this adhesive stretches under the edge of the carrier sheet for providing a better sealing and protection of a hydrocolloid adhesive.

In a further embodiment of the invention, the thickness of the adhesive wafer of the body side member is smaller in the area next to the central hole for accommodating the stoma for further facilitating the rolling thereof In a preferred embodiment of the invention the first adhesive surface of the body side member is covered with a release liner having an indication of the size of the hole of an ostomy appliance of the invention for accommodating a stoma, at the surface in contact with the adhesive (distal as compared to the ostomy) for facilitating a customisation of the hole. In the alternative, the indication may be placed on the side facing away from the body side member (proximal as compared to the ostomy) if the release liner is transparent. In an especially preferred embodiment of the invention a customised cutting guide as the one disclosed in WO 00/25709 is used.

In a preferred embodiment of the invention the part of the adhesive wafer surrounding the stoma is in the form of an exchangeable sealing member disposed in the hole of the wafer and having a hole for accommodating a stoma. This allows for a larger period of time between exchanges of the body side member itself reducing the stress posed on the skin.

A body side member of the invention is preferably provided with coupling means for releasable attachment of a receiving bag.

The coupling means may be any system known per se for attaching receiving bags to ostomy body side members and may suitably be matching coupling rings of the type disclosed in WO 93/18725 or WO 94/18919 or matching flanges for adhesive connection of the type disclosed in U.S. Pat. No. 5,800,415.

It is preferred that the coupling means are matching coupling rings.

A coupling ring may e.g. be attached to the carrier sheet by adhesive means or preferably by welding In another aspect the invention relates to an ostomy sealing member in the form of a mouldable mass or ring having a first adhesive surface which shows a sufficient adhesiveness to adhere to the skin and to seal around a stoma and between the stoma and an ostomy appliance adapted to receive secretions from the stoma, which sealing member has a second surface facing away from the user optionally being covered by a top film, said sealing member having a hole for accommodating a stoma and said sealing member having balanced plastic and elastic properties allowing an enlarging of the hole for receiving a stoma by rolling up the inner rim of the hole forming a torus before placing the sealing member around the stoma and wherein a part of the second surface surrounding the hole shows surface properties compatible with the first adhesive surface locking the torus to the second surface in its rolled position by the contact between the second surface and the first adhesive surface.

The adhesive surfaces of a sealing member of the invention are suitably covered by release liners to be removed before application as discussed above.

In a third aspect the invention relates to an ostomy appliance comprising an adhesive wafer having a first adhesive surface for securing the appliance to the user's skin, said wafer having a second surface being covered with a carrier sheet to which a receiving bag is secured, which wafer has a hole for receiving a stoma wherein the part of the adhesive wafer surrounding the stoma shows balanced plastic and elastic properties allowing an adaptation of the size of the hole of the ostomy appliance to a stoma by enlarging the hole by rolling up the inner rim thereof for accommodating the stoma forming a torus and wherein the second surface of a part of the wafer surrounding the hole shows properties compatible with the first adhesive surface of the adhesive wafer locking the torus to the second surface in its rolled position by the contact between the second surface and the first adhesive surface.

In a preferred embodiment of the invention a separator piece located between the carrier sheet and the adhesive. Such a separator sheet is preferably located in the central part of the adhesive wafer and may be used as temporary support during rolling of the edge of the hole of a base plate, a sealing member or an ostomy appliance of the invention. In one embodiment of the invention, the separator piece is provided with a weakening zone in the form of a cut defining a central part of the separator piece, which part may be detached separately. Such a weakening zone may be provided as disclosed above. In a preferred embodiment of the invention the separator piece has an indication of the size of the hole of an ostomy appliance of the invention for accommodating a stoma as indicated above.

A separator piece may suitably be made form a material such as polyethylene, polypropylene or a polyester sheet and it is also considered an aspect of the invention to use a degradable material, especially in open bags for intermittent emptying in order to prevent a blocking of the outlet.

In a fourth aspect the invention relates to a method of applying an ostomy appliance body side member comprising an adhesive wafer having a first adhesive surface for securing the appliance to a user's skin and a second surface being covered with a carrier sheet and a hole for receiving a stoma wherein a part of the adhesive wafer surrounding the stoma shows balanced plastic and elastic properties allowing an adaptation of the size of the hole of the ostomy appliance to a stoma by enlarging the hole by rolling up the inner rim thereof for accommodating the stoma and having an inner rim, and wherein the second surface of a part of the wafer surrounding the hole shows properties compatible with the first adhesive surface of the adhesive wafer locking the torus to the second surface in its rolled position by the contact between the second surface and the first adhesive surface, said method comprising enlarging the hole by rolling the inner rim of the hole adapting of the hole to the size of the stoma forming a torus, locking the torus to the second surface in its rolled position by contact between the second surface and the first adhesive surface, aligning the stoma and the hole of the ostomy appliance body side member for accommodating the stoma and placing the body side member on the abdomen of the ostomate with the stoma projecting into the hole.

In a fifth aspect the invention relates to a method of applying an ostomy appliance body side member comprising an adhesive wafer having a first adhesive surface for securing the appliance to a user's skin and a second surface being covered with a carrier sheet and a first hole comprising a sealing member in the form of a mouldable mass or ring having a first adhesive surface which shows a sufficient adhesiveness to adhere to the skin and to seal around a stoma and between the stoma and the ostomy body side member, which sealing member has a second surface facing away from the user optionally being covered by a top film and a second hole for accommodating a stoma, and having an inner rim, and said sealing member having balanced plastic and elastic properties allowing an enlarging of the second hole for receiving a stoma by rolling up the inner rim thereof for accommodating the stoma forming a torus, and wherein a part of the second surface of the sealing member surrounding the hole shows properties compatible with the first adhesive surface of the adhesive sealing member locking the torus to the second surface in its rolled position by the contact between the second surface and the first adhesive surface, said method comprising a) locating the stoma and aligning the stoma and the hole of the body side member and placing the body side member on the abdomen of the ostomate with the stoma projecting into the hole, b) enlarging the hole of the sealing member by rolling the inner rim of the hole of the sealing member forming a torus, c) adapting the hole to the size of the stoma, d) locking the torus to the second surface of the sealing member in its rolled position by contact between the adhesive surface and the second surface of the sealing member, e) aligning the stoma and the second hole of the ostomy sealing member and f) placing the same in the first hole of the body side member on the abdomen of the ostomate with the stoma projecting into the second hole.

In a sixth aspect the invention relates to a method of applying a one-piece ostomy appliance comprising an adhesive wafer having a first adhesive surface for securing the appliance to the user's skin, said wafer having a second surface being covered with a carrier sheet to which a receiving bag is secured, which wafer has a hole for receiving a stoma and having an inner rim, wherein a part of the adhesive wafer surrounding the stoma shows balanced plastic and elastic properties allowing an adaptation of the size of the hole of the ostomy appliance to a stoma by enlarging the hole by rolling up the inner rim thereof for accommodating the stoma forming a torus, and wherein the second surface of a part of the wafer surrounding the hole shows properties compatible with the first adhesive surface of the adhesive wafer locking the torus to the first surface in its rolled position by the contact between the second surface and the first adhesive surface, said method comprising enlarging the hole by rolling the inner rim of the hole adapting of the hole to the size of the stoma forming a torus, locking the torus to the first surface in its rolled position by contact between the second surface and the first adhesive surface, aligning the stoma and the hole of the ostomy appliance for accommodating the stoma and placing the ostomy appliance on the abdomen of the ostomate with the stoma projecting into the hole.

An ostomy body side member or an ostomy appliance according to the invention may be produced from standard materials normally used for preparation of disposable ostomy and wound and incontinence devices. Thus, the carrier sheet may be any suitable thermoplastic material known per se for use in the preparation of ostomy appliances e.g. a foam, a non-woven layer or a polyurethane, polyethylene, polyester or polyamide film and the adhesive wafer itself may be made from a medical grade barrier adhesives comprising hydrocolloids known in the art such as the formulations being disclosed, for example in U.S. Pat. Nos. 4,367,732, 5,051,259 or 5,714,225.

An adhesive wafer suitably comprises an adhesive, which absorbs humidity such as perspiration. A second adhesive material may be formulated without hydrocolloids or using a minor amount of hydrocolloids or using a material such as potato starch which has been found to have a low absorbing capacity when formulated in medical adhesives in order to ensure that a second adhesive preferably shows a lower absorption in order to prolong the service time of a product of the invention.

In accordance with a preferred embodiment of the invention an adhesive wafer assembly for use for the manufacture of an ostomy body side member or an ostomy appliance of the invention is made using the technology disclosed in EP Patent No. 1 117 516 providing a suitable manner for producing multi layered products comprising discrete components such as a separator piece. Thus, a product according to the invention having a separator piece located between the carrier sheet and the adhesive may be produced in analogy with the method disclosed in EP 1 117 516 by placing a separator sheet on the carrier sheet before dispensing the adhesive.

A receiving bag for use with a body side member or an ostomy appliance of the invention may be known per se and comprise front and rear walls sealed together along the rim and provided with an inlet opening may be made in analogy with and from materials conventionally used for the preparation of ostomy appliances.

Such materials are suitably films composed of any suitable material, which is heat sealable and sufficiently impervious for unpleasant odours such as polyolefin films or combinations of such films, e.g. polyethylene or a coextrudate of polyethylene and polyvinylidene chloride.

A protective cover or release liner may for instance be siliconized paper. It does not need to have the same contour as body side member, e.g. a number of body side members or especially sealing members may be attached to a larger sheet of protective cover. The protective cover is not present during the use of the ostomy appliance of the invention and is therefore not an essential part of the invention.

In a preferred embodiment of the invention the protective cover or release liner is provided with a weakening zone in the form of a cut defining a central part of the release liner which may be detached separately leaving the remaining part of the release liner on the adhesive surface.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The invention is now explained more in detail with reference to the drawings showing preferred embodiments of the invention.

Reference is made to FIG. 1 which shows a cross sectionally view of an ostomy body side member 1 of the state of the art comprising an adhesive wafer 2 having a first surface for securing the appliance to the user's skin S, said wafer having a second surface being covered by a carrier sheet 3 conventionally used, e.g. a LDPE or a PU film, which wafer has a hole for receiving a stoma wherein the part of the adhesive wafer surrounding the stoma shows balanced plastic and elastic properties allowing an adaptation of the size of the hole of the ostomy appliance to a stoma by enlarging the hole by rolling up the inner rim thereof for accommodating the stoma. Furthermore, the body side member is provided with a coupling ring 4 for attachment of a receiving bag provided with a matching coupling ring and a release liner 5 for protecting the first adhesive surface until use.

Figure 2:
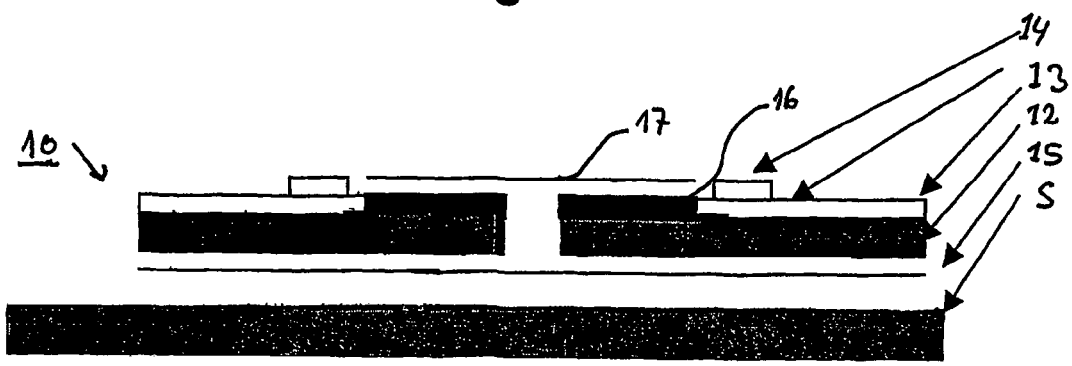
FIG. 2 shows a cross sectional view of an embodiment of a body side member according to the invention.

FIG. 2 shows a cross sectional view of an embodiment of an ostomy appliance body side member 10 according to the invention comprising an adhesive wafer 12 having a first adhesive surface for securing the appliance to the user's skin S, said adhesive having a second surface being covered by a carrier sheet 13 conventionally used for ostomy appliances. Furthermore, the body side member is provided with a coupling ring 14 for attachment of a receiving bag and a release liner 15 for protecting the first adhesive surface until use. The carrier sheet is absent on a central part of the second surface of the adhesive wafer 12 surrounding the stoma. The body side member comprises a second layer of adhesive 16 disposed on the second surface of the wafer surrounding the stoma and stretching under the inner rim of the carrier sheet 13 and a release liner 17 covering said second layer of adhesive. The release liner is to be removed before application of the appliance. A receiving bag provided with a matching coupling ring may be secured to the coupling ring in a manner known per se.

Figure 3:
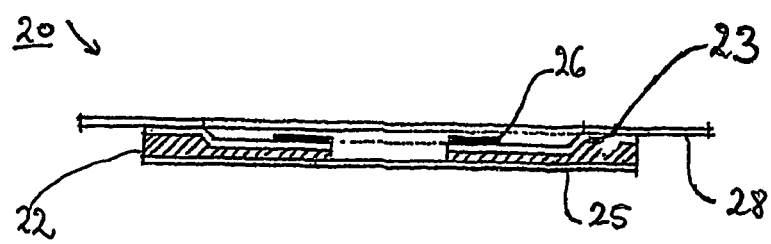
FIG. 3 shows a cross sectional view of an embodiment of a sealing member according to the invention.

FIG. 3 shows a cross sectional view of a sealing member 20 of the present invention comprising an adhesive wafer 22, having a carrier sheet 23 having mechanical properties similar to the adhesive. The wafer is thinner in the area next to the central hole for accommodating the stoma and is provided with a release liner 25 for protecting the adhesive surface until use. The sealing member comprises a second layer of adhesive 26, preferably a hydrophobic adhesive layer, disposed on the second distal surface of the member surrounding the stoma. The sealing member is furthermore provided with a flange part 28 for attaching the sealing member to the surface of a body side member.

Figure 4:
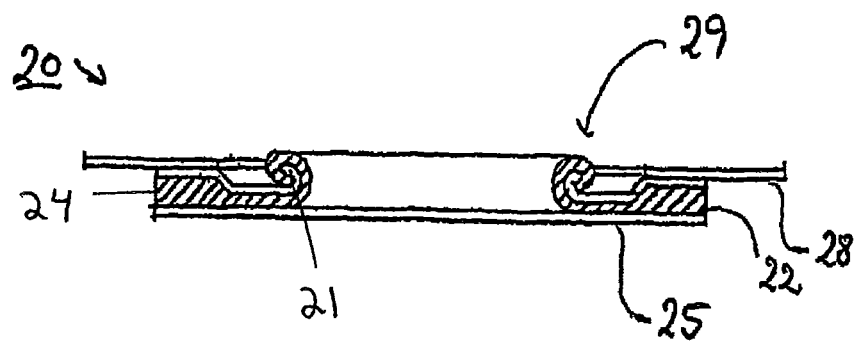
FIG. 4 shows a cross sectional view of the embodiment of FIG. 3 wherein the inner rim of a sealing member has been rolled up.

In FIG. 4, the adhesive wafer 22 extends from an inner rim 21 that forms the central hole to an outer rim 24. The inner rim 21 has been rolled up forming a torus 29, revealing a larger part of the surface of the release liner 25 below, which provides an indication of the size of the hole as illustrated in FIG. 5.

Figure 5:
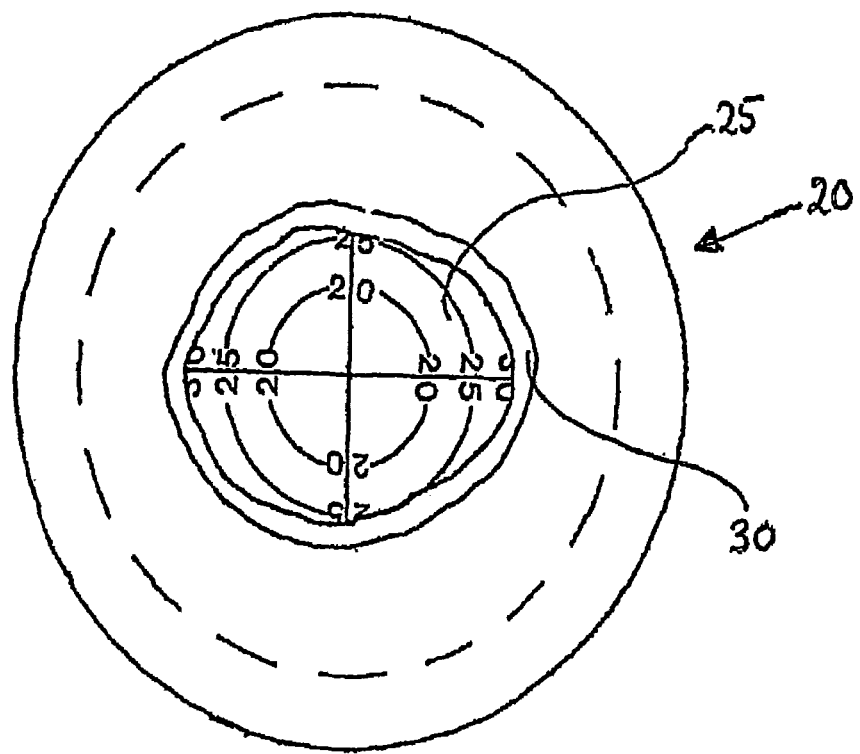
FIG. 5 shows a view from the distal side of the separate sealing member of FIG. 3 in which the inner rim thereof has been partially rolled up to increase the size of the hole of an ostomy appliance of the invention and showing the indication of the size of the hole placed on a release liner below.

FIG. 5 shows a top view from the distal side of a separate sealing member 20 of the invention having a hole for accommodating a stoma in which the rim of the hole has been partially rolled for forming the torus into a shape 30 to fit an irregular stoma and showing the indication of the size of the hole placed on a release liner 25 visible through the hole.

Figure 6:
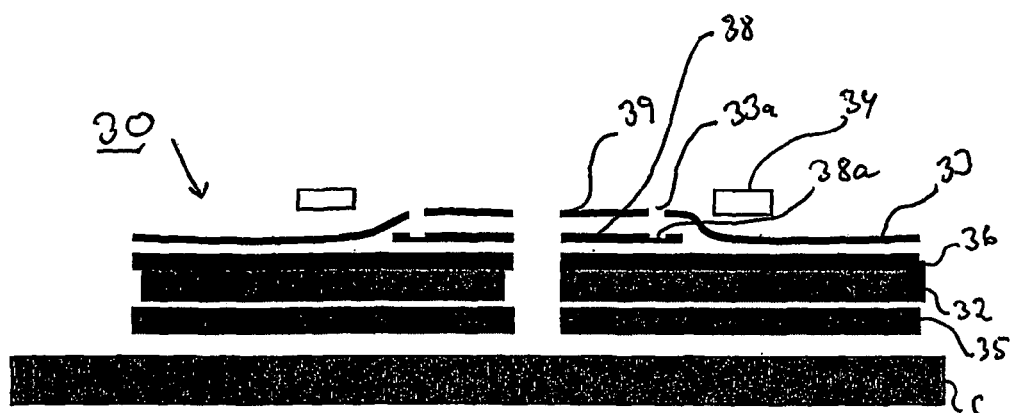
FIG. 6 shows an exploded cross sectional view of a second embodiment of a body side member of the invention.

FIG. 6 shows an exploded sectional view of a second embodiment of a body side member 30 according to the invention comprising an adhesive wafer 32 having a first adhesive surface for securing the appliance to the user's skin S, said adhesive having a second surface being covered by a carrier sheet 33 conventionally used for ostomy appliances. Furthermore, the body side member is provided with a coupling ring 34 for attachment of a receiving bag and a release liner 35 for protecting the first adhesive surface until use. The carrier sheet is provided with a weakening zone in the form of a cut 33a defining a central part 39 of the carrier sheet, which may be detached separately. The body side member comprises a second layer of adhesive 36 disposed on the second surface of the wafer surrounding the stoma and stretching under the inner rim of the carrier sheet 33 and a separator piece 38 covering the central part of the second layer of adhesive. Furthermore, the separator piece on the central part of the carrier sheet is provided with a weakening zone in the form of a cut 38a defining a central part of the separator piece 38, which may be detached separately. The central part of the carrier sheet may be removed when manufacturing the base plate or immediately before the use. When preparing the base plate for use, the user or an assistant removes the central part of the separator piece, optionally bending the base plate to produce a break in the weakening lines and then rolls the edge of the hole forming a torus and adapting the size of the hole to the stoma. Alternatively, the rim of the separator piece may simply slip from below the carrier sheet on bending. This may be done using a table as support, whereafter the release liner is removed and the base plate applied to the user and a receiving bag provided with a matching coupling ring may be secured to the coupling ring in a manner known per se.

Figure 7:
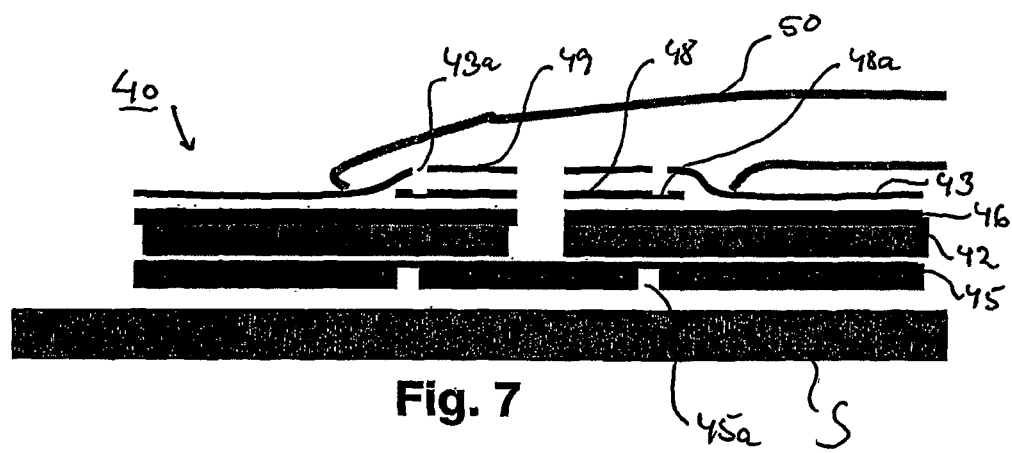
FIG. 7 shows an exploded cross sectional view of a one-piece ostomy appliance according to the invention.
Figure 8:
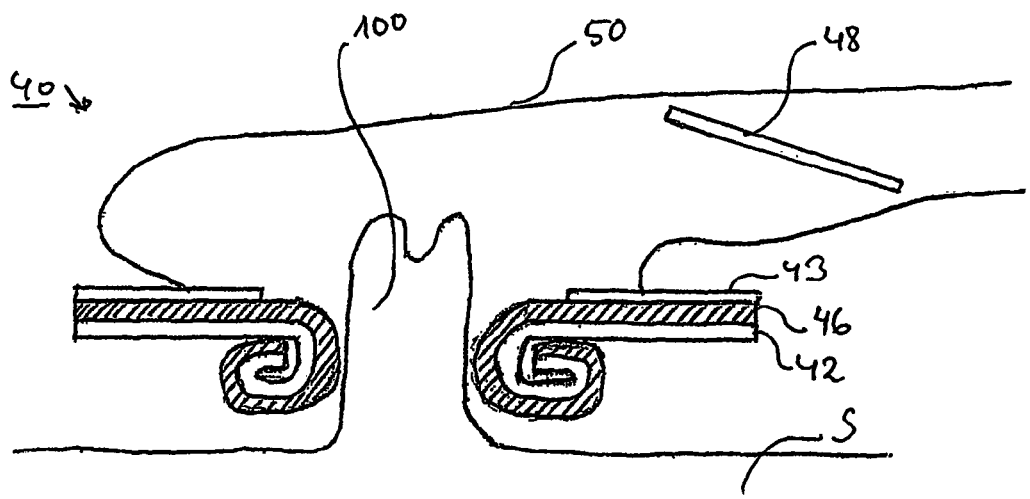
FIG. 8 shows a cross sectional view of the embodiment of FIG. 7 wherein the inner rim of a sealing member has been rolled up.

FIGS. 7 and 8 illustrate a one-piece ostomy appliance according to the invention. FIG. 7 shows an exploded cross sectional view of an embodiment of an ostomy appliance 40 according to the invention comprising an adhesive wafer 42 having a first adhesive surface for securing the appliance to the user's skin S, said adhesive having a second surface being covered by a carrier sheet 43 conventionally used for ostomy appliances. Furthermore, the appliance is provided with a receiving bag 50 and a release liner 45 for protecting the first adhesive surface until use. The carrier sheet is provided with a weakening zone in the form of a cut 43a defining a central part 49 of the carrier sheet, which may be detached separately. The appliance comprises a second layer of adhesive 46 disposed on the second surface of the wafer surrounding the stoma and stretching under the inner rim of the carrier sheet 43 and a separator piece 48 covering the central part of the second layer of adhesive. Furthermore, the separator piece on the central part of the carrier sheet is provided with a weakening zone in the form of a cut 48a defining a central part of the separator piece 48, which may be detached separately. The central part of the carrier sheet may be removed when manufacturing the base plate before securing the bag 50.

Furthermore, the release liner 45 is provided with a weakening zone in the form of a cut 45a defining a central part of the release liner which may be detached separately leaving the remaining part of the release liner on the adhesive surface. When preparing the appliance for use, the user or an assistant removes the central part of the release liner, optionally bending the appliance to produce a break in the weakening lines and then rolls the edge of the hole outwards forming a torus and adapting the size of the hole to the stoma. This may be done using a table as support, and the separator piece protects the bag from adhering to an adhesive surface during this process. Then the separator piece is punched into the bag, the remaining part of the release liner is removed, and the appliance is applied to the user.

FIG. 8 shows a cross sectional view of the embodiment of FIG. 7 wherein the inner rim of a sealing member has been rolled up during application around the stoma 100 and with the separator piece located in the bag.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method of applying a separately exchangeable ostomy sealing member in a body side member, said sealing member having balanced plastic and elastic properties and including an inner rim that defines a first hole for accommodating a stoma, a first moisture-absorbing adhesive surface adapted for securing the sealing member to an ostomate's abdomen and for receiving secretions from the stoma, and a second surface facing away from the user, a central part of the second surface of said sealing member surrounding said first hole being provided with a hydrophobic adhesive layer compatible with the first adhesive surface of the adhesive wafer and having an adhesive upper surface covered by a release liner provided as a separator sheet that is covered by a carrier sheet, said carrier sheet having a weakening zone defining a central part of said carrier sheet that is positioned over said separator sheet and that is removable separately while a remainder of said carrier sheet including an inner rim thereof remains in place to allow the separator sheet to be removed to expose the adhesive upper surface of said hydrophobic adhesive layer, the method comprising:

a) locating the stoma and aligning the stoma and a second stoma-accommodating hole of the body side member and placing the body side member on the abdomen of the ostomate with the stoma projecting into the second hole;

b) removing the release liner from said adhesive upper surface of the hydrophobic adhesive layer;

c) enlarging the first hole of the sealing member by rolling the inner rim of the hole of the sealing member toward an outer perimeter of the sealing member;

d) adapting the first hole of the sealing member to the size of the stoma;

e) adhering the first adhesive surface to the hydrophobic adhesive layer of the second surface of the sealing member;

f) aligning the stoma and the second hole of the ostomy sealing member; and g) placing the sealing member in the second hole of the body side member on the abdomen of the ostomate with the stoma projecting into the first hole.

2. The body side member as claimed in claim 1 wherein an outer edge of said separator sheet extends under the inner rim of said carrier sheet, said separator sheet including a weakening zone that defines a central part of said separator sheet that can be removed separately while said separator sheet outer edge remains in place under said carrier sheet inner rim.

3. The body side member as claimed in claim 2 wherein said weakening zones are defined by cuts in said sheets.

4. An ostomy appliance body side member comprising:

an adhesive wafer extending between an outer rim and an inner rim defining a hole for accommodating a stoma and including a first adhesive surface attachable to a user's skin and a second adhesive surface opposite the first adhesive surface;

a removable release liner disposed over a portion of the second adhesive surface; and a carrier sheet disposed on the second adhesive surface over at least a portion of the removable release liner, a portion of the carrier sheet removable to expose a portion of the second adhesive surface and leave a remainder of the carrier sheet in place;

wherein the hole for accommodating the stoma is enlarged by rolling the inner rim of the adhesive wafer toward the outer rim and adhering the first adhesive surface to the exposed portion of the second adhesive surface.

* * * * *